United States Patent [19]
Jung et al.

[11] Patent Number: 6,046,342
[45] Date of Patent: Apr. 4, 2000

[54] 3, 6-BIS[4-(ALKYLOXY) PHENYLOXY] PYROMELLITIC DIANHYDRIDES AND PROCESS FOR PREPARING THE SAME

[75] Inventors: Jin Chul Jung, Seoul; Kyung-Hoon Lee, Pohang, both of Rep. of Korea

[73] Assignee: Korea Advanced Institute of Science and Technology, Taejon, Rep. of Korea

[21] Appl. No.: 09/275,487

[22] Filed: Mar. 24, 1999

[30] Foreign Application Priority Data

Jun. 17, 1998 [KR] Rep. of Korea ............... 98-22740

[51] Int. Cl.⁷ .................................. C07D 493/02
[52] U.S. Cl. .......................................... 549/239
[58] Field of Search ........................ 549/239, 233

[56] References Cited

U.S. PATENT DOCUMENTS 3,431,240  3/1969  Vogel et al. .................... 260/49

OTHER PUBLICATIONS

D. Brandelik, "Polymides Baed on 3,6–Diphenoxypyromellitic Dianhydride", Poymer Preprints, 28(1), pp. 888–889 (1987).

F.W. Harris and S. Hsu, "Synthesis and Characterization of Polymides Based on 3,6–Diphenylpyromellitic Dianhydride", High Performance Polymers, 1(1), pp. 3–16 (1989).

Kyung Hoon Lee and Jin Chul Jung, "Synthesis and Characterization of Polymides from 1,4–bis[4–(n–alkyloxy)phenyloxy]pyromellitic dianhydrides and 4,4'–oxydianiline", Polymer Bulletin, 40(4);pp. 407–414 (1998).

Kyung Hoon Lee and Jin Chul Jung, "Synthesis and Characterization of Polymides from 3,6–Bis[4–(n–alkyloxy)phenyloxy]Pyromellitic Dianhydrides and 4,4'–Oxydianiline", Abstracts, presented at the Polymer Society of Korea, Apr. 10–11, 1998.

Kyung Hoon Lee and Jin Chul Jung, "Synthesis of Novel Polyimides Having 4–(n–Alkyloxy)phenyloxy Side Chains", Abstracts, presented at the Polymer Society of Korea, Oct. 16–17, 1998.

Tohru Matsurura et al., "Polyimides Derived from 2,2'–is(trifluoromethyl)–4,4'–diaminobiphenyl. 2. Synthesis and Characterization of Polyimides Prepared from Fluorinated Benzenetetracarboxylic Dianhydrides", Macromolecules, 25(13), pp. 3540–3545 (1992).

*Primary Examiner*—John Kight
*Assistant Examiner*—Charanjit S. Aulakh
*Attorney, Agent, or Firm*—Knobbe, Martens, Olson & Bear, LLP

[57] ABSTRACT

The present invention provides pyromellitic dianhydride derivatives represented as formula I:

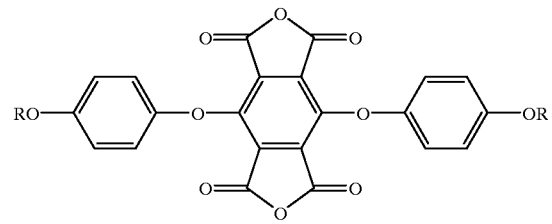

Formula I wherein,

R is $C_{1-24}$ alkyl.

The pyromellitic dianhydride derivatives of the invention can be used as monomers for the synthesis of polyimides, ladder poly(imidazopyrrolone)s, crosslinked polyamides and polyesters. The present invention also provides a novel process for preparing the pyromellitic dianhydride derivatives as formula I.

11 Claims, No Drawings

3, 6-BIS[4-(ALKYLOXY) PHENYLOXY] PYROMELLITIC DIANHYDRIDES AND PROCESS FOR PREPARING THE SAME

This application claims the priority benefit of Foreign application No. 98-22740 filed Jun. 17, 1998.

FIELD OF THE INVENTION

The present invention relates to novel pyromellitic dianhydride derivatives which possess a broad spectrum of potential applications as dianhydride monomers to prepare high-temperature polymers with distinctively enhanced solubilities and process for preparing these compounds.

BACKGROUND OF THE INVENTION

Pyromellitic dianhydride is commercially available and widely used as the monomer for preparing a variety of linear, ladder, or crosslinked high-temperature polymers with excellent thermal, thermomechanical, thermooxidative and radiation resistances by polymerization with aromatic di- or polyfunctional amines. Linear polyimides, ladder poly(imidazopyrrolone)s and crosslinked polyesters and polyamides are representative Examples of such polymers. Polyimides are of particular importance and widely used in industry as thermally stable films, liquid crystal alignment layers, semiconductor coatings, or flexible printed circuit boards.

However, the poly(pyromellitimide)s prepared by polycondensation with aromatic diamines have only poor solubilities or fusibilities, and they have mostly been processed via precursor processing methods. To improve the processabilities of the polyimides, incorporation of organic substituents at 3- and 6-positions of pyromellitic dianhydride has been attempted and 3,6-bis(Q)pyromellitic dianhydrides have been developed, where Q is bromo, fluoro, chloro, trifluoromethyl, phenyl or oxyphenyl. In spite of the presence of these substituents, no distinctive improvement of the processability compared to poly(pyromellitimide)s has been observed.

Therefore, needs have been existed for the development of new pyromellitic dianhydride derivatives which provide, when polymerized with the same aromatic diamines, distinctively more improved processabilities of the polyimides than the unsubstituted poly(pyromellitimide)s or poly[3,6-bis(Q)pyromellitimide]s.

SUMMARY OF THE INVENTION

The present inventors have discovered that incorporation of alkyloxy groups at 4-position of the phenyl group of 3,6-bis(oxyphenyl)pyromellitic dianhydride (Q=oxyphenyl) meets the above requirements and further that the larger the alkyl groups, the better the solubilities of the corresponding polyimides.

A primary object of the present invention is, therefore, to provide 3,6-bis[4-(alkyloxy)phenyloxy]pyromellitic dianhydrides.

The other object of the invention is to provide a process for preparing the said compounds.

DETAILED DESCRIPTION OF THE INVENTION

The novel pyromellitic dianhydride derivatives of the present invention are represented as the following formula I:

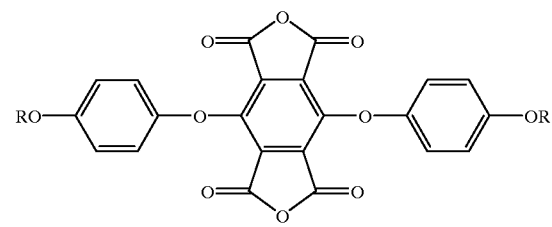

Formula I wherein,

R is $C_{1-24}$ linear alkyl, preferably, methyl, ethyl, n-propyl, isopropyl, n-butyl, isobutyl, t-butyl n-pentyl, isopentyl, 3-methylpentyl, n-hexyl, isohexyl, 2-ethylhexyl, n-heptyl, isoheptyl, n-octyl, isooctyl, n-nonyl, n-decyl, isodecyl, n-undecyl, isoundecyl, n-dodecyl, isododecyl, n-tetradecyl, n-hexadecyl, n-octadecyl, n-eicosyl, n-docosyl, or n-tetracosyl, more preferably, methyl, ethyl, n-propyl, isopropyl, n-butyl, isobutyl, n-hexyl, 2-ethylhexyl, n-heptyl, isoheptyl, n-octyl, n-decyl, n-dodecyl, n-hexadecyl, n-octadecyl, n-eicosyl or n-tetracosyl.

3, 6-bis[4-(alkyloxy)phenyloxy]pyromellitic dianhydrides of the invention represented by formula I can be prepared by the process which comprises the following steps:

Step I: Nucleophilic substitution

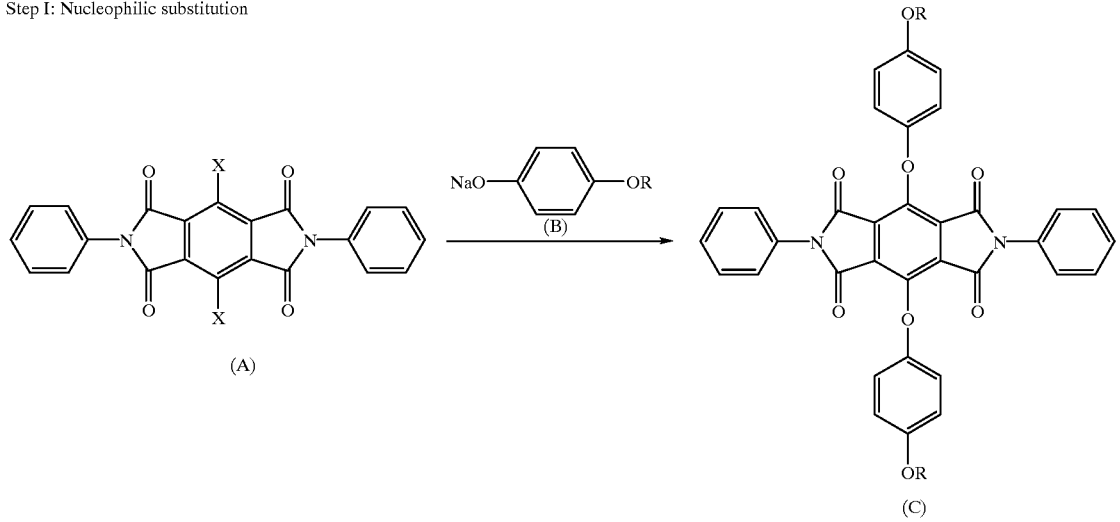

wherein,

X is F, Cl, Br or I; and,

R is $C_{1-24}$ alkyl described as above.

N,N'-diphenyl-3-6-bis(halogeno)pyromellitic diimides (A) and sodium 4-(alkyloxy)phenolates(B) are dissolved in an organic solvent and reacted in the presence or absence of a strong organic or inorganic base to obtain N,N'-diphenyl-3,6-bis[4-(alkyloxy)phenyloxy]pyromellite diimides(C) for 1 to 72 hrs. As preferred organic solvent is used a highly purified polar solvent such as dimethylsulfoxide, N,N'-dimethylformamide, N,N'-dimethylacetamide, N-methylpyrrolidone, 1,2-dimethoxyethane, hexamethylphosphoramide and the like.

The preferred base used is an organic strong base such as pyridine, trimethylamine, triethylamine, tributylamine, N,N'-dimethylaniline, triethylenediamine and the like or an inorganic strong base such as NaH, $NaOCH_3$, $NaOC_2H_5$, $NaO(n-C_4H_7)$, NaOH, KOH, $Na_2CO_3$ and the like.

The reaction of (A) with (B) is conducted preferably at a temperature ranging from −60° C. to the boiling point of the solvent when X is F or I, and at a temperature ranging from −40° C. to the boiling point of the solvent when X is Br or Cl.

Step II: Hydrolysis

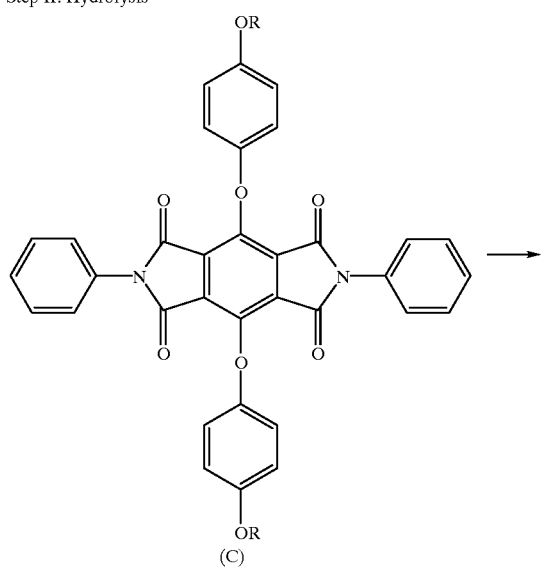

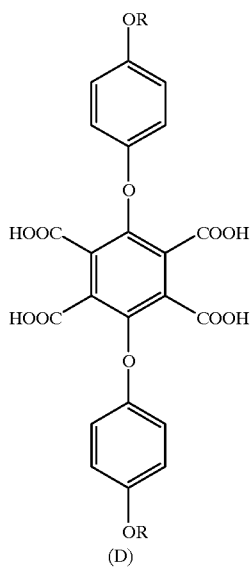

wherein,

R is $C_{1-24}$ alkyl group described as above.

N,N'-diphenyl-3,6-bis[4-(alkyloxy)phenyloxy] pyromellitic diimides(C) are hydrolyzed by acidic or basic catalysts to obtain 3,6-bis[4-(alkyloxy)phenyloxy] pyromellitc acids(D). The preferred method of hydrolysis was a basic hydrolysis with NaOH. After (C) is basically hydrolyzed, the hydrolyzed solutions are acidified with a dilute mineral acid to obtain (D). The preferred mineral acid is hydrochloric acid.

Step III: Cyclodehydration

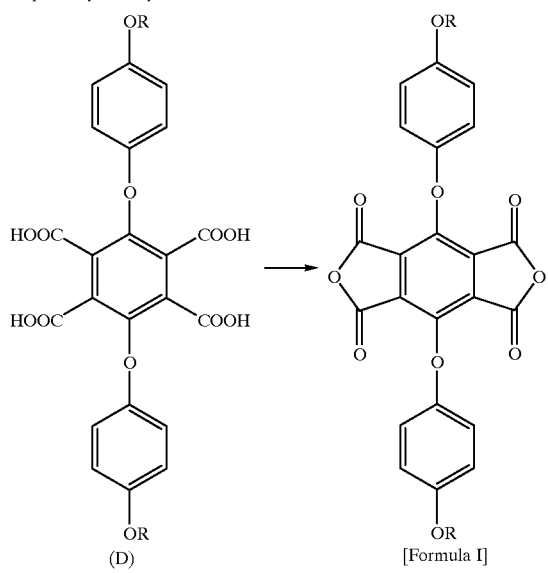

wherein,

R is $C_{1-24}$ alkyl group described as above.

3,6-bis[4-(alkyloxy)phenyloxy]pyromellitic dianhydrides of the present invention are obtained by dehydrating cyclization reaction of 3,6-bis[4-(alkyloxy)phenyloxy]pyromellitic acids(D). The dehydrating cyclization reactions are carried out preferably by treating thermally in vacuum or chemically with acetic anhydride.

The following Preparation Examples are intended to further illustrate synthetic process of the present invention, without limiting the scope of the invention.

PREPARATION EXAMPLE 1

Synthesis of N,N'-diphenyl-3,6-bis[4-(methyloxy) phenyloxy]pyromellitic Diimide

Into 100 ml of pure N-methylpyrrolidone were dissolved 4.04 g (10 mmol) of N,N'-diphenyl-3,6-difluoropyromellitic diimide and 3.21 g (22 mmol) of sodium 4-(methyloxy) phenolate. This solution was stirred for 24 hr at room temperature under nitrogen purging and heated to 100° C. for 2 hr. After cooled to ambient temperature, it was poured to 600 ml distilled water. When this aqueous solution was neutralized with dilute HCl, red precipitates were formed. These precipitates were filtered, air-dried and recrystallized from ethyl acetate to obtain the desired compound, N,N'-diphenyl-3,6-bis[4-(methyloxy)phenyloxy]pyromellitic diimide (yield: 95%).

Melting point: 381° C. IR (KBr, cm$^{-1}$): 1774 & 1726 (imide I), 1596 & 1508 (aromatic C=C), 1396 (imide II), 1255 & 1193 (C—O—C) $^1$H-NMR (DMSO-d$_6$, δ ppm): 3.70 (s, 6H), 6.85, 6.88, 7.06, 7.09 (dd, 8H, aromatic), 7.36~7.51 (m, 10H, aromatic)

PREPARATION EXAMPLE 2

Synthesis of 3,6-bis[4-(methyloxy)phenyloxy] pyromellitic Acid

Into 150 ml of 10% NaOH solution made from a 1:1 (v:v) mixture of ethanol and distilled water were dissolved 2 g of N,N'-diphenyl-3,6-bis[4-(methyloxy)phenyloxy] pyromellitic diimide obtained from preparation Example 1. The solution was refluxed for 72 hr under nitrogen atmosphere and then cooled to ambient temperature. When it was neutralized with 5% aqueous HCl, white precipitates were formed. These precipitates were filtered, air-dried and recrystallized from 1:1 (v:v) mixture of hexane and ethyl acetate to obtain the desired compound, 3,6-bis[4-(methyloxy)phenyloxy]pyromellitic acid (yield: 85%).

Neutralization value: 449 mg KOH/g IR (KBr, cm$^1$): 3600~2300 (br, COOH), 1737 & 1697 (C=O), 1506 (aromatic), 1224 & 1176 (C—O—C) $^1$H-NMR (DMSO-d$_6$, δ ppm): 3.70 (s, 6H), 6.75, 6.78, 6.85, 6.88 (dd, 8H, aromatic), 13.5 (br, COOH)

PREPARATION EXAMPLE 3

Synthesis of 3,6-bis[4-(methyloxy)phenyloxy] pyromellitic Dianhydride 1 g of 2,6-bis[4-(methyloxy)phenyloxy]pyromellitic acid obtained in Preparation Example 2 was dissolved into 15 ml of acetic anhydride. This solution was refluxed for 6 hr under nitrogen purging and then cooled to ambient temperature. After the liquid was evaporated by vacuum, the remaining solids were recrystallized from toluene to obtain the desired product, 3,6-bis[4-(methyloxy)phenyloxy]pyromellitic dianhydride (yield: 94%).

Melting point: 296° C. IR (KBr, cm$^{-1}$): 1851, 1830~1780 (C=O), 1600 & 1510 (aromatic C=C), 1257 & 1190 (C—O—C) $^1$H-NMR (acetone-d$_6$, δ ppm): 3.77 (s, 6H), 6.87, 6.90, 7.08, 7.11 (dd, 8H, aromatic)

PREPARATION EXAMPLE 4

Synthesis of N,N'-diphenyl-3,6-bis[4-(methyloxy) phenyloxy]pyromellitic Diimide

Into 100 ml of purified N,N'-dimethylacetamide were dissolved 5.2 g (10 mmol) of N,N'-diphenyl-3,6-dibromopyromellitic diimide and 3.21 g (22 mmol) of sodium 4-(methyloxy)phenolate. Under nitrogen purging this solution was slowly heated to 150° C. in 1 hr, reacted for 24 hr at this temperature and then cooled to ambient temperature. When this solution was dropped to 600 ml distilled water and neutralized with dilute HCl, red precipitates were formed. These precipitates were filtered, air-dried and recrystallized from ethyl acetate to obtain the desired product, N,N'-diphenyl-3,6-bis[4-(methyloxy)phenyloxy] pyromellitic diimide (yield: 83%).

Melting point: 381° C. IR (KBr, cm$^{-1}$): 1774 & 1726 (imide I), 1596 & 1508 (aromatic C=C), 1396 (imide II), 1255 & 1193 (C—O—C) $^1$H-NMR (DMSO-d$_6$, δ ppm): 3.70 (s, 6H), 6.85, 6.88, 7.06, 7.09 (dd, 8H, aromatic), 7.36~7.51 (m, 10H, aromatic)

PREPARATION EXAMPLE 5

Synthesis of 3,6-bis[4-(ethyloxy)phenyloxy] pyromellitic Dianhydride

Into 100 ml of thoroughly dried dimethylsulfoxide were dissolved 5.26 g (10 mmol) of N,N'-diphenyl-3,6-dibromopyromellitic diimide and 3.52 g (22 mmol) of sodium 4-(ethyloxy)phenolate. Under gentle nitrogen flow this solution was slowly heated to 150° C. in 1 hr and reacted for 24 hr at this temperature. After cooled to ambient temperature this solution was dropped to 600 ml distilled water. When this aqueous solution was neutralized with dilute HCl, red precipitates were formed. These precipitates were filtered, air-dried and recrystallized from ethyl acetate to obtain N,N'-diphenyl-3,6-bis[4-(ethyloxy)phenyloxy] pyromellitic diimide.

Into 150 ml of 10% NaOH solution made from 1:1 (v:v) mixture of ethanol and water were dissolved 2 g N,N'-diphenyl-3,6-bis[4-(ethyloxy)phenyloxy]pyromellitic diimide obtained from above. This solution was refluxed for 72 hr under nitrogen atmosphere and then cooled to ambient temperature. When the cooled solution was neutralized with 5% aqueous HCl, white precipitates were formed. These were filtered, air-dried and recrystallized from 1:1 (v:v) mixture of hexane and ethyl acetate to obtain 3,6-bis[4-(ethyloxy)phenyloxy3-pyromellitic acid.

1 g of 2,6-bis[4-(ethyloxy)phenyloxy]pyromellitic acid obtained from above was dissolved into 15 ml of acetic anhydride. This solution was refluxed for 6 hr under nitrogen purging and cooled to ambient temperature. After the liquid was evaporated by vacuum, the remaining solids were recrystallized from toluene to obtain pure 3,6-bis[4-(ethyloxy)phenyloxy]pyromellitic dianhydride.

Total yield: 58% Melting point: 287° C. Neutralization value: 487 mg KOH/g IR (KBr, cm$^{-1}$): 2970~2870 (CH), 1851, 1830 & 1780 (C=O), 1600 & 1510 (aromatic C=C), 1257 & 1190 (C—O—C) $^1$H-NMR (acetone-d$_6$, δ ppm): 0.91~0.95, (t, 6H), 3.70~3.77 (q, 4H), 6.87, 6.90, 7.80, 7.11 (dd, 8H, aromatic)

PREPARATION EXAMPLE 6

Synthesis of 3,6-bis[4-(n-butyloxy)phenyloxy] pyromellitic Dianhydride

Into 100 ml of thoroughly dried dimethylsulfoxide were dissolved 5.26 g (10 mmol) of N,N'-diphenyl-3,6-dibromopyromellitic diimide and 4.09 g (22 mmol) of sodium 4-(n-buthyloxy)phenolate. Under gentle nitrogen flow this solution was stirred for 72 hr at ambient temperature and further reacted at 100° C. for 2 hr. After cooled to ambient temperature this solution was dropped to 600 ml distilled water. When this aqueous solution was neutralized with dilute HCl, red precipitates were formed. These precipitates were filtered, air-dried and recrystallized from ethyl acetate to obtain N,N'-diphenyl-3,6-bis[4-(n-butyloxy) phenyloxy]pyromellitic diimide.

Into 150 ml of 10% NaOH solution made from 1:1 (v:v) mixture of ethanol and water were dissolved 2 g of N,N'-diphenyl-3,6-bis[4-(n-butyloxy)phenyloxy]pyromellitic diimide obtained from above. This solution was refluxed for 72 hr under nitrogen atmosphere and then cooled to ambient temperature. When it was neutralized with 5%, aqueous HCl, white precipitates were formed. These precipitates were filtered, air-dried and recrystallized from 1:1 (v:v) mixture of hexane and ethyl acetate to obtain 3,6-bis[4-(n-butyloxy)phenyloxy]pyromellitic acid.

1 g of 2,6-bis[4-(n-butyloxy)phenyloxy]pyromellitic acid obtained from above was dissolved into 15 ml of acetic anhydride. This solution was refluxed for 6 hr under nitrogen purging and cooled to ambient temperature. After the liquid was evaporated by vacuum, the remaining solids were recrystallized from toluene to obtain pure 3,6-bis[4-(n-butyloxy)phenyloxy]pyromellitic dianhydride.

Total yield: 63% Melting point: 264° C. Neutralization value: 412 mg KOH/g IR (KBr, cm$^{-1}$): 2976~2872 (CH), 1857, 1830 & 1799 (C=O), 1600 & 1506 (aromatic C=C), 1247 & 1193 (C—O—C), 720 (-(CH$_2$)$_4$-) $^1$H-NMR (acetone-d$_6$, δ ppm): 0.93~0.97 t, 6H) 1.44~1.51 (sext, 4H), 1.68~1.75 (quint, 4H), 3.93~3.98 (t, 4H), 6.87, 7.06, 7.09 (dd, 8H, aromatic)

PREPARATION EXAMPLE 7

Synthesis of 3,6-bis[4-n-octyloxy)phenyloxy] pyromellitic Dianhydride

Into a mixture from 100 ml of pure N,N'-dimethylacetamide and 1 ml of tributylamine were dissolved 5.26 g (10 mmol) of N,N'-diphenyl-3,6-dibromopyromellitic diimide and 5.37 g (22 mmol) of sodium 4-(n-octyloxy) phenolate. Under nitrogen flow this solution was stirred for 72 hr at ambient temperature. When it was dropped to 600 ml distilled water and neutralized with dilute HCl, red precipitates were formed. These precipitates were filtered, air-dried and recrystallized from ethyl acetate to obtain N,N'-diphenyl-3,6-bis[4-(n-octyloxy)phenyloxy] pyromellitic diimide.

Into 150 ml of 10% NaOH solution made from 1:1 (v:v) mixture of ethanol and water were dissolved 2 g of N,N'-diphenyl-3,6-bis[4-(n-octyloxy)phenyloxy]pyromellitic diimide obtained from above. This solution was refluxed for 72 hr under nitrogen atmosphere and then cooled to ambient temperature. When it was neutralized with 5% aqueous HCl, white precipitates were formed. These precipitates were filtered, air-dried and recrystallized from 1:1 (v:v) mixture of hexane and ethyl acetate to obtain 3,6-bis[4-(n-octyloxy)phenyloxy]pyromellitic acid.

1 g of 2,6-bis[4-(n-octyloxy)phenyloxy]pyromellitic acid obtained from above was dissolved into 15 ml of acetic anhydride. This solution was refluxed for 6 hr under nitrogen purging and cooled to ambient temperature. After the liquid was evaporated by vacuum, the remaining solids were recrystallized from toluene to obtain sure 3,6-bis[4-(n-octyloxy)phenyloxy]pyromellitic dianhydride.

Total yield: 66% Melting point: 235° C. Neutralization value: 342 mg KOH/g IR (KBr, cm$^{-1}$): 2976~2848 (CH), 1853, 1830 & 1784 (C=O), 1600 & 1504 (aromatic C=C), 1249 & 1190 (C—O—C), 722 (-(CH$_2$)$_4$-) $^1$H-NMR (acetone-d$_6$, δ ppm): 0.86~0.90 (t, 6H), 1.30~1.46 (sext, 4H), 1.72~1.77 (quint, 4H), 3.93~3.97 (t, 4H), 6.86, 6.89, 7.06, 7.09 (dd, 8H, aromatic)

PREPARATION EXAMPLE 8

Synthesis of 3,6-bis[4-(n-dodecyloxy)phenyloxy]-pyromellitic Dianhydride

Into a mixture from 150 ml of pure 1,2-dimethoxyethane and 1 ml of tributylamine were dissolved 5.2 g (10 mmol) N,N'-diphenyl-3,6-dibromopyromellitic diimide and 6.60 g (22 mmol) of sodium 4-(n-dodecyloxy)phenolate. Under nitrogen flow this solution was stirred for 72 hr at −20° C. and then warmed to ambient temperature. When it was dropped to 600 ml distilled water and neutralized with dilute HCl, red precipitates were formed. These precipitates were filtered, air-dried and recrystallized from ethyl acetate to obtain N,N'-diphenyl-3,6-bis[4-(n-dodecyloxy)phenyloxy] pyromellitic diimide.

Into 150 ml of 10% NaOH solution made from 1:1 (v:v) mixture of ethanol and water were dissolved 2 g of N,N'-diphenyl-3,6-bis[4-(n-dodecyloxy)phenyloxy]pyromellitic diimide obtained from above. This solution was refluxed for 72 hr under nitrogen atmosphere and then cooled to ambient temperature. When it was neutralized with 5% aqueous HCl, white precipitates were formed. These precipitates were filtered, air-dried and recrystallized from 1:1 (v:v) mixture of hexane and ethyl acetate to obtain 3,6-bis[4-(n-dodecyloxy)phenyloxy]pyromellitic acid.

1 g of 2,6-bis[4-(n-dodecyloxy)phenyloxy]pyromellitic acid obtained from above was dissolved into 15 ml of acetic anhydride. This solution was refluxed for 6hr under nitrogen purging and cooled to ambient temperature. After the liquid was evaporated by vacuum, the remaining solids were recrystallized from toluene to obtain pure 3,6-bis[4-(n-dodecyloxy)phenyloxy]pyromellitic dianhydride.

Total yield: 64% Melting point: 220° C. Neutralization value: 290 mg KOH/g IR (KBr, cm$^{-1}$): 2976~2850 (CH), 1849, 1811 & 1774 (C=O), 1598 & 1506 (aromatic C=C), 1249 & 1184 (C—O—C), 724 (-(CH$_2$)$_4$-) $^1$H-NMR (acetone-d$_6$, δ ppm): 0.85~0.90 (t, 6Hz, 1.41~1.46 (br, 36H), 1.72~1.77 (quint, 4H), 3.93~3.97 (t, 4H), 6.86, 6.89, 7.06, 7.09 (dd, 8H, aromatic)

PREPARATION EXAMPLE 9

Synthesis of 3,6-bis[4-(n-tetracosyloxy)phenyloxy] pyromellitic Dianhydride

Into a mixture from 200 ml of pure 1,2-dimethoxyethane and 2 ml of pyridine were dissolved 5.26 g (10 mmol) of N,N'-diphenyl-3,6-dibromopyromellitic diimide and 10.30 g (22 mmol) of sodium 4-(n-tetracosyloxy)phenolate. Under nitrogen flow this solution was stirred for 72 hr at ambient temperature. When it was dropped to 600 ml distilled water and neutralized with dilute HCl, red precipitates were formed. These precipitates were filtered, air-dried and recrystallized from ethyl acetate to obtain N,N'-diphenyl-3, 6-bis[4-(n-tetracosyloxy)phenyloxy]pyromellitic diimide.

Into 150 ml of 10% NaOH solution made from 1:1 (v:v) mixture of ethanol and water were dissolved 2 g of N,N'-diphenyl-3,6-bis[4-(n-tetracosyloxy)phenyloxy] pyromellitic diimide obtained from above. This solution was refluxed for 72 hr under nitrogen atmosphere and then cooled to ambient temperature. When it was neutralized with 5% aqueous HCl, white precipitates were formed. These were filtered, air-dried and recrystallized from 1:1 (v:v) mixture of hexane and ethyl acetate to obtain 3,6-bis[4-(n-tetracosyloxy)phenyloxy]pyromellitic acid.

1 g of 2,6-bis[4-(n-tetracosyloxy)phenyloxy]pyromellitic acid obtained from above was dissolved into 15 ml of acetic anhydride. This solution was refluxed for 6 hr under nitrogen purging and cooled to ambient temperature. After the liquid was evaporated by vacuum, the remaining solids were recrystallized from toluene to obtain pure 3,6-bis[4-(n-tetracosyloxy)phenyloxy]pyromellitic dianhydride.

Total yield: 64% Melting point: 220° C. Neutralization value: 290 mg KOH/g IR (KBr, cm$^{-1}$): 2976~2850(CH), 1849, 1811 & 1774 (C=O), 1598 & 1506 (aromatic C=C), 1249 & 1184 (C—O—C), 724 (-(CH$_2$)$_4$-) $^1$H-NMR (acetone-d$_6$, δ ppm): 0.85~0.90 (t, 6H), 1.41~1.46 (br, 36H), 1.72~1.77 (quint, 4H), 3.93~3.97 (t, 4H), 6.86, 6.89, 7.06, 7.09 (dd, 8H, aromatic)

PREPARATION EXAMPLE 10

Synthesis of 3,6-bis[4-(t-butyloxy)phenyloxy] pyromellitic Dianhydride

Into a mixture from 100 ml of pure N,N'-dimethylformamide and 3 ml of tributylamine were dissolved 5.26 g (10 mmol) of N,N'-diphenyl-3,6-dibromopyromellitic diimide and 4.09 g (22 mmol) of sodium 4-(t-butyloxy)phenolate. Under nitrogen flow this solution was stirred for 72 hr at ambient temperature and then for 2 hr at 100° C. After cooled to ambient temperature this solution was dropped to 600 ml distilled water. When this aqueous solution was neutralized with dilute HCl, red precipitates were formed. These precipitates were filtered, air-dried and recrystallized from ethyl acetate to obtain N,N'-diphenyl-3,6-bis[4-(t-butyloxy)phenyloxy] pyromellitic diimide.

Into 150 ml of 10% NaOH solution made from 1:1 (v:v) mixture of ethanol and water were dissolved 2 g of N,N'-diphenyl-3,6-bis[4-(t-butyloxy)phenyloxy]pyromellitic diimide obtained from above. This solution was refluxed for 72 hr under nitrogen atmosphere and then cooled to ambient temperature. When it was neutralized with 5% aqueous HCl, white precipitates were formed. These precipitates were filtered, air-dried and recrystallized from 1:1 (v:v) mixture of hexane and ethyl acetate to obtain 3,6-bis[4-(t-butyloxy) phenyloxy]pyromellitic acid.

1 g of 2,6-bis(4-(t-butyloxy)phenyloxy]pyromellitic acid obtained from above was dissolved into 15 ml of acetic anhydride. This solution was refluxed for 6 hr under nitrogen purging and cooled to ambient temperature. After the liquid was evaporated by vacuum, the remaining solids were recrystallized from toluene to obtain pure 3,6-bis[4-(t-butyloxy)phenyloxy]pyromellitic dianhydride.

Total yield: 60% Melting point: 258° C. Neutralization value: 413 mg KOH/g IR (KBr, cm$^{-1}$): 2978~2870 (CH), 1860, 1830 & 1800 (C=O), 1600 & 1506 (aromatic C=C), 1247 & 1193 (C—O—C) $^1$H-NMR (acetone-d$_6$, δ ppm): 0.92 (s, 18H), 6.85, 6.90, 7.04, 7.07 (dd, 8H, aromatic)

PREPARATION EXAMPLE 11

Synthesis of 3,6-bis[2-ethylhexyloxy)phenyloxy] pyromellitic Dianhydride

Into a mixture from 100 ml of pure N,N'-dimethylformamide and 1 ml of tri(n-butyl)amine were dissolved 5.26 g (10 mmol) N,N'-diphenyl-3,6-dibromopyromellitic diimide and 5.37 g (22 mmol) of sodium 4-(2-ethylhexyloxy)phenolate. Under nitrogen flow this solution was stirred for 72 hr at ambient temperature. When this solution was dropped to 60 ml distilled water and neutralized with dilute HCl, red precipitates were formed. These precipitates were filtered, air-dried and recrystallized from ethyl acetate to obtain N,N'-diphenyl-3,6-bis[4-(2-ethylhexyloxy)phenyloxy]pyromellitic diimide.

Into 150 ml of 10% NaOH solution made from 1:1 (v:v) mixture of ethanol and water were dissolved 2 g of N,N'-diphenyl-3,6-bis[4-(2-ethylhexyloxy)phenyloxy] pyromellitic diimide obtained from above. This solution was refluxed for 72 hr under nitrogen atmosphere and then cooled to ambient temperature. When this solution was neutralized with 5% aqueous HCl, white precipitates were formed. These precipitates were filtered, air-dried and recrystallized from 1:1 (v:v) mixture of hexane and ethyl acetate to obtain 3,6-bis[4-(2-ehtylhexyloxy)phenyloxy] pyromellitic acid.

1 g of 2,6-bis[4-(2-ethylhexyloxy)phenyloxy] pyromellitic acid obtained from above was dissolved into 15 ml of acetic anhydride. This solution was refluxed for 6 hr under nitrogen purging and then cooled to ambient temperature. After the liquid was evaporated by vacuum, he remaining solids were recrystallized from toluene to obtain pure 3,6-bis[4-(t-butyloxy)phenyloxy]pyromellitic dianhydride.

Total yield: 54% Melting point: 232° C. Neutralization value: 343 mg KOH/g IR (KBr, cm$^{-1}$): 2976~2846 (CH), 1855, 1830 & 1786 (C=O), 1600 & 1504 (aromatic C=C), 1250 & 1190 (C—O—C), 724 (-(CH$_2$)$_4$-) $^1$H-NMR (acetone-d$_6$, δ ppm): 0.86~0.90 (t, 12H), 1.30~1.68 (br, 18H), 3.96~4.01 (d, 4H), 6.86, 6.89, 7.06, 7.09 (dd, 8H, aromatic)

The following Use Examples are intended 0 illustrate useful application of the compounds of the present invention as monomers for preparing polyimides.

USE EXAMPLE 1

Synthesis of poly{4,4'-biphenylene-3,6-bis[4-(n-butyloxy)phenyloxy]pyromellitimide}

Into 50 ml of N-methylpyrrolidone were dissolved 5.46 g (10 mmol) of 3,6-bis[4-(n-butyloxy)phenyloxy]pyromellitic dianhydride and 1.84 g (10 mmol) of 4,4'-diaminobiphenyl. Under nitrogen purging this solution was violently stirred for 60 hr at ambient temperature. As the polymerization reaction proceeds, the solution became viscous.

To the viscous solution were added 30 ml of acetic anhydride and 1 ml of triethylamine and stirred for further 24 hr at ambient temperature under nitrogen purging. When this solution was dropped to 500 ml ethanol under violent stirring, reddish precipitates were formed. After these precipitates were filtered and air-dried, they were thoroughly extracted by refluxing in 50 ml ethanol for 24 hr and then filtered. Drying the filtered polymers at 130° C. in vacuum for 24 hr gave poly{4,4'-biphenylene-3,6-bis[4-(n-butyloxy) phenyloxy]pyromellitimide}.

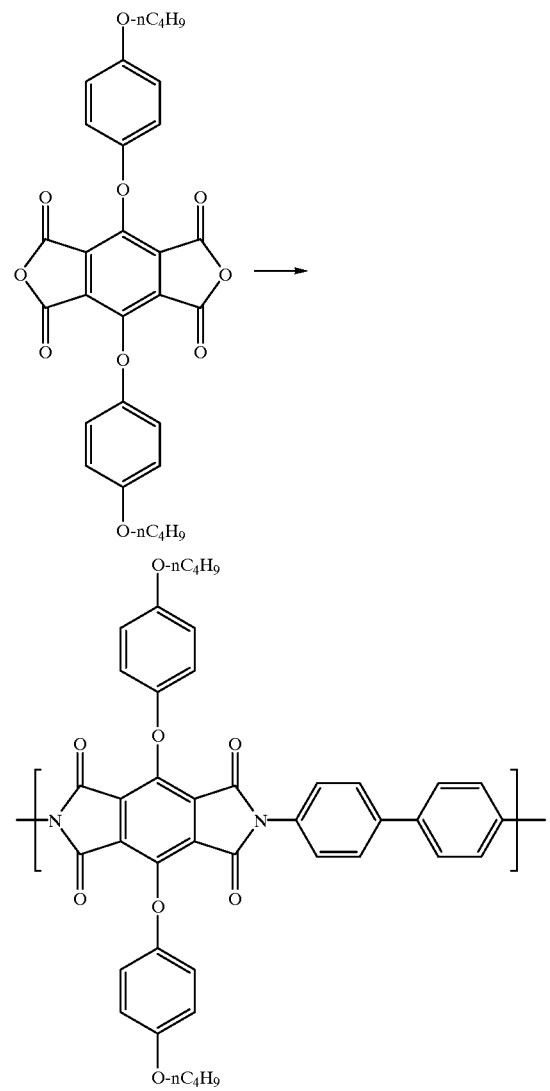

Yield: 99% Inherent viscosity (25° C., 0.1 g/dl, N-methylpyrrolidone): 2.29 dl/g Elemental analysis: C, 71.58%; H, 5.21%; N, 4.23%; IR (KBr, cm$^{-1}$): 2954~2850 (CH), 1772 & 1728 (imide I), 1608 & 1504 (aromatic C=C), 1390 (imide II), 1242 & 1182 (C—O—C)

USE EXAMPLE 2

Synthesis of poly{4,4'-biphenylene-3,6-bis[4-(n-dodecyloxy)phenyloxy]pyromellitimide}

Into 100 ml of N,N'-dimethylacetamide were dissolved 7.70 g (10 mmol) of 3,6-bis[4-(n-dodecyloxy)phenyloxy] pyromellitic dianhydride and 1.84 g (10 mmol) of 4,4'-diaminobiphenyl. Under nitrogen purging this solution was violently stirred for 72 hr at ambient temperature. As the polymerization reaction proceeds, the solution became viscous.

To the viscous solution were added 30 ml of acetic anhydride and 1 ml of triethylamine and stirred for further 24 hr at ambient temperature under nitrogen purging. When this solution was dropped to 500 ml ethanol under violent stirring, reddish precipitates were formed. After these precipitates were filtered and air-dried, they were thoroughly extracted by refluxing in 50 ml ethanol for 24 hr and then filtered. Drying the filtered polymers at 100° C. in vacuum for 24 hr gave poly{4,4'-biphenylene-3,6-bis [4-(n-dodecyloxy)phenyloxy]pyromellitimide}.

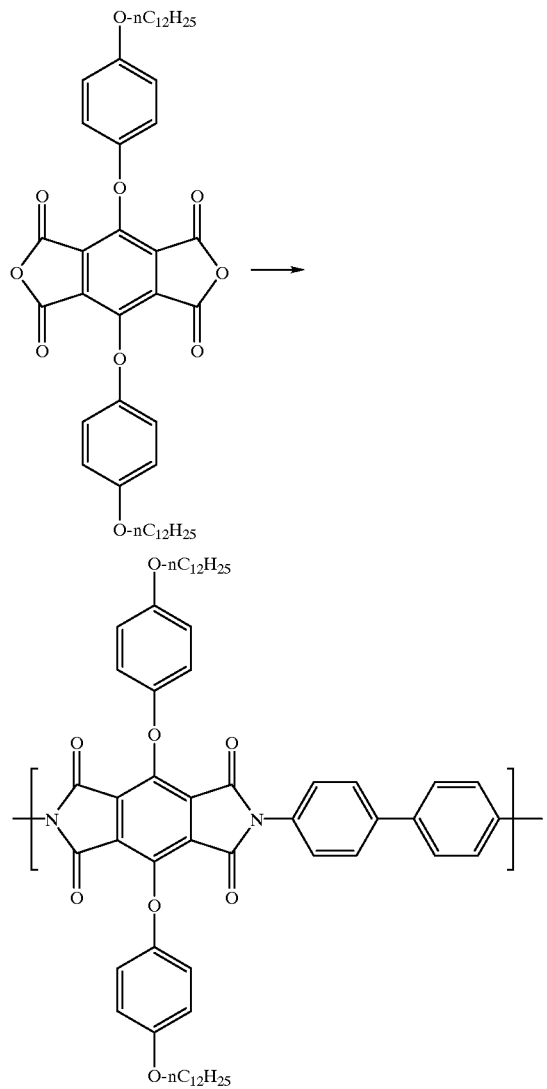

Yield: 99% Elemental analysis: C, 74.31%; H, 7.01%; N, 2.49%; IR (KBr, cm$^{-1}$): 2921~2860 (CH), 1776 & 1728 (imide I), 1608 & 1504 (aromatic C=C), 1392 (imide II), 1244 & 1186 (C—O—C), 725 (-(CH$_2$)$_4$-)

USE EXAMPLE 3

Synthesis of poly{1,4-phenylene-3,6-bis[4-(n-tetracosyloxy)phenyloxy]pyromellitimide}

Into 100 ml of 1,2-dimethylacetamide were dissolved 11.06 g (10 mmol) of 3,6-bis[4-(n-tetracosyloxy)phenyloxy] pyromellitic dianhydride and 1.08 g (10 mmol) of 1,4-phenylenediamine. Under nitrogen purging this solution was violently stirred for 72 hr at ambient temperature. As the polymerization reaction proceeds, the solution became viscous.

To the viscous solution were added 50 ml of acetic anhydride and 1 ml of triethylamine and stirred for further 24 hr at ambient temperature under nitrogen purging. When this solution was dropped to 800 ml ethanol under violent stirring, reddish precipitates were formed. After these precipitates were filtered and air-dried, they were thoroughly extracted by refluxing in 100 ml ethanol for 24 hr and then filtered. Drying the filtered polymers at 100° C. in vacuum for 24 hr gave poly{4,4'-biphenylene-3,6-bis[4-(n-tetracosyloxy)phenyloxy]pyromellitimide}.

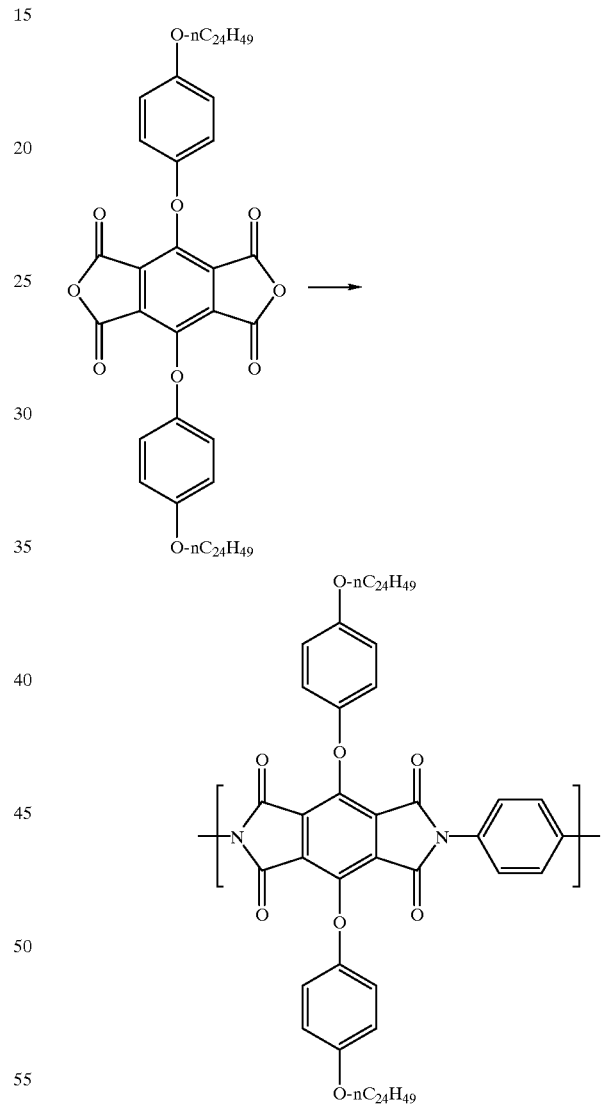

Yield: 99% Elemental analysis: C, 79.68%; H, 5.17%; N, 2.65%; IR (KBr, cm$^{-1}$) : 2936~2858 (CH), 1778 & 1734 (imide I), 1604 & 1504 (aromatic C=C), 1392 (imide II), 1250 & 1190 (C—O—C), 725 (-(CH$_2$)$_4$-)

USE EXAMPLE 4

Synthesis of poly{1,4-phenylene-3,6-bis[4-(n-dodecyloxy)phenyloxy]pyromellitimide}

Into 100 ml of 1,2-dimethoxyethane were dissolved 7.70 g (10 mmol) of 3,6-bis[4-(n-dodecyloxy)phenyloxy]

pyromellitic dianhydride and 1.08 g (10 mmol) of 1,4-phenylenediamine. Under nitrogen purging this solution was violently stirred for 72 hr at ambient temperature. As the polymerization reaction proceeds, the solution became viscous.

To the viscous solution were added 50 ml of acetic anhydride and 1 ml of triethylamine and stirred for further 24 hr at ambient temperature under nitrogen purging. When this solution was dropped to 800 ml ethanol under violent stirring, reddish precipitates were formed. After these precipitates were filtered and air-dried, they were thoroughly extracted by refluxing in 100 ml ethanol for 24 hr and then filtered. Drying the filtered polymers at 100° C. in vacuum for 24 hr gave poly{1,4'-phenylene-3,6-bis[4-(n-dodecyloxy)phenyloxy]pyromellitimide}.

pyromellitic dianhydride and 2.12 g (10 mmol) of 3,3'-dimethyl-4,4'-diaminobiphenyl. Under nitrogen purging this solution was violently stirred or 72 hr at ambient temperature. As the polymerization reaction proceeds, the solution became viscous.

To the viscous solution were added 30 ml of acetic anhydride and 1 ml of triethylamine and stirred for further 24 hr at ambient temperature under nitrogen purging. When this solution was dropped to 500 ml ethanol under violent stirring, reddish precipitates were formed. After these precipitates were filtered and air-dried, they were thoroughly extracted by refluxing in 50 ml ethanol for 24 hr and then filtered. Drying the filtered polymers at 130° C. in vacuum for 24 gave poly{4,4'-(3,3'-dimethyl)biphenylene-3,6-bis[4-(n-butyloxy)phenyloxy]pyromellitimide}.

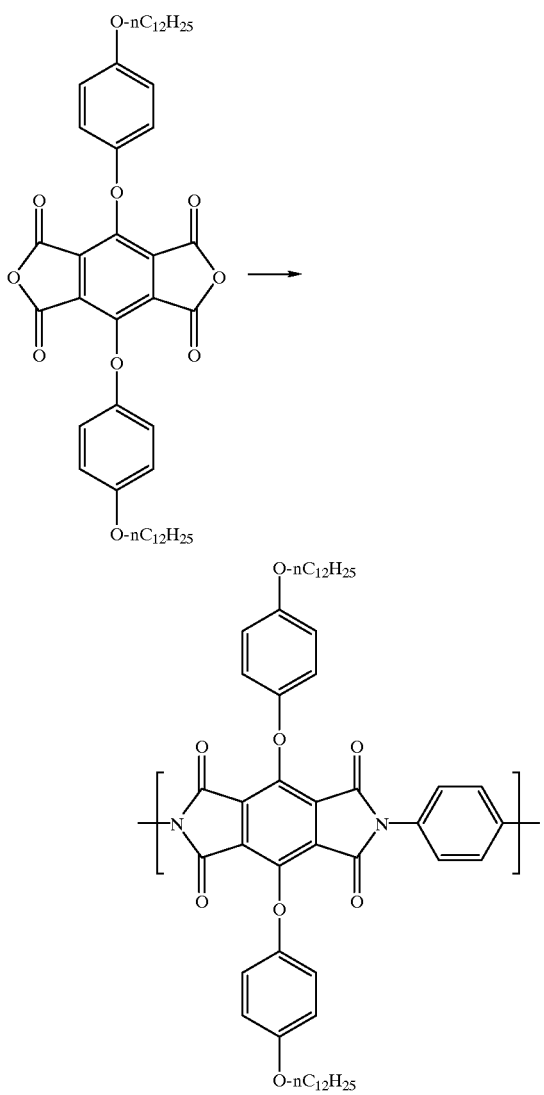

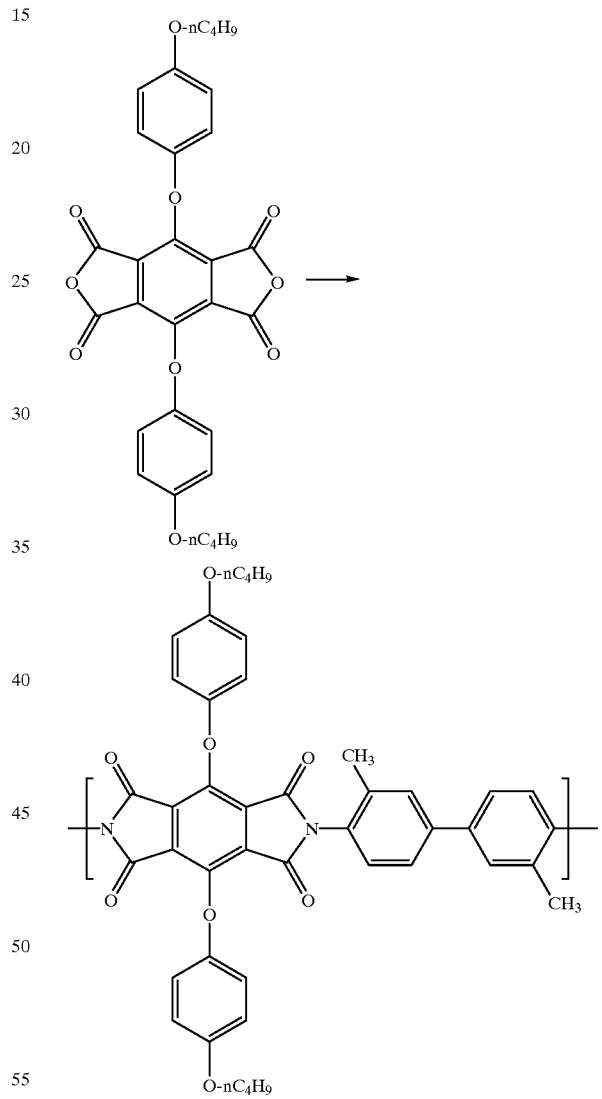

Yield: 99% Elemental analysis: C, 73.11%; H, 7.27%; N, 3.29%; IR (KBr, cm⁻): 2930~2856 (CH), 1776 & 1735 (imide I), 1598 & 1504 (aromatic C=C), 1390 (imide II), 1244 & 1186 (C—O—C), 725 (-(CH$_2$)$_4$-)

USE EXAMPLE 5

Synthesis of poly{4,4-(3,3'-dimethyl)biphenylene-3,6-bis[4-(n-butyloxy)phenyloxy]pyromellitimide}

Into 500 ml of N,N'-dimethylformamide were dissolved 5.46 g (10 mmol) of 3,6-bis[4-(n-butyloxy)phenyloxy]

Yield: 99% Inherent viscosity (25° C., N-methylpyrrolidone, 0.2 g/dl): 0.66 dl/g Elemental analysis: C, 71.75%; H, 5.30%; N, 4.49%; IR (KBr, cm⁻¹): 2960~2872 (CH), 1774 & 1730 (imide I), 1610 & 1504 (aromatic C=C), 1388 (imide II), 1244 & 1184 (C—O—C), 725 (-(CH$_2$)$_4$-)

USE EXAMPLE 6

Synthesis of poly{4,4'-(3,3'-dimethyl)biphenylene-3,6-bis[4-(n-octyloxy)phenyloxy]pyromellitimide}

Into 80 ml of hexamethylphosphoramide were dissolved 6.58 g (10 mmol) of 3,6-bis[4-(n-octyloxy)phenyloxy]

pyromellitic dianhydride and 2.12 g (10 mmol) of 3,3'-dimethyl-4,4'-diaminobiphenyl. Under nitrogen purging this solution was violently stirred for 72 hr at ambient temperature. As the polymerization reaction proceeds, the solution became viscous.

To the viscous solution were added 30 ml of acetic anhydride and 1 ml of triethylamine and stirred for further 24 hr at ambient temperature under nitrogen purging. When this solution was dropped to 500 ml ethanol under violent stirring, reddish precipitates were formed. After these precipitates were filtered and air-dried, they were thoroughly extracted by refluxing in 50 ml ethanol for 24 hr and then filtered. Drying the filtered polymers at 100° C. in vacuum for 24 hr gave poly{4,4'-(3,3'-dimethyl)biphenylene-3,6-bis[4-(n-octyloxy)phenyloxy]pyromellitimide}.

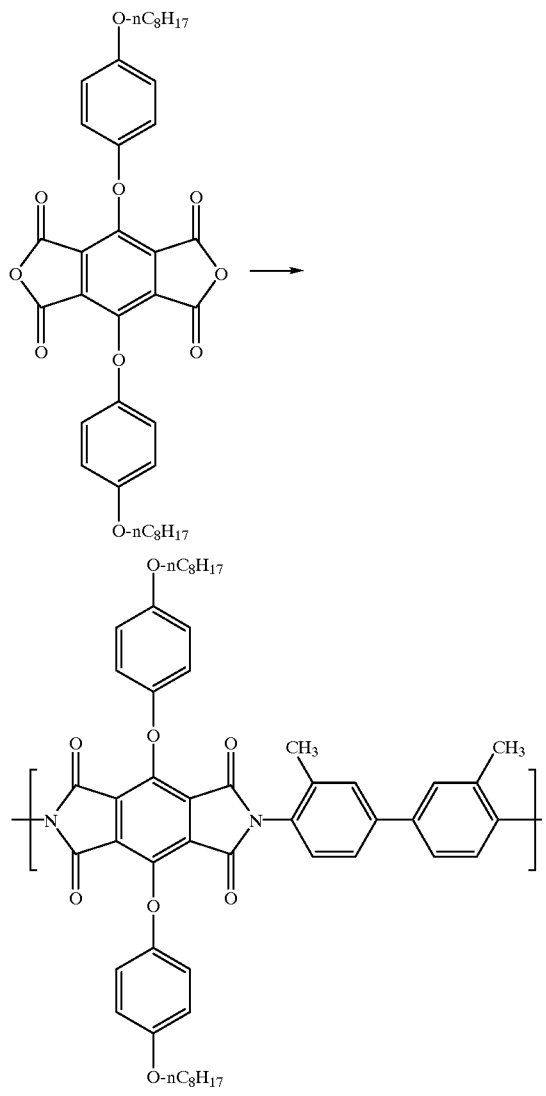

Yield: 99% Inherent viscosity (25° C., N-methylpyrrolidone, 0.2 g/dl): 0.56 dl/g Elemental analysis: C, 74.18%; H, 6.57%; N, 4.15% ;

IR (KBr, cm$^{-1}$): 2928~2856 (CH), 1776 & 1731 (imide I), 1610 & 1504 (aromatic C=C), 1390 (imide II), 1245 & 1186 (C—O—C), 724 (-(CH$_2$)$_4$-)

USE EXAMPLE 7

Synthesis of poly{1,4-phenyleneoxy-1,4-phenylene-3,6-bis[4-(n-octyloxy)phenyloxy]pyromellitimide}

Into 80 ml of N-methylpyrrolidone were dissolved 6.58 g (10 mmol) of 3,6-bis[4-(n-octyloxy)phenyloxy]pyromellitic dianhydride and 2.00 g (10 mmol) of 4,4'-oxydianiline. Under nitrogen purging this solution was violently stirred for 72 hr at ambient temperature. As the polymerization reaction proceeds, the solution became viscous.

To the viscous solution were added 50 ml of acetic anhydride and 1 ml of triethylamine and stirred for further 24 hr at ambient temperature under nitrogen purging. When this solution was dropped to 600 ml ethanol under violent stirring, reddish precipitates were formed. After these precipitates were filtered and air-dried, they were thoroughly extracted by refluxing in 80 ml ethanol for 24 hr and then filtered. Drying the filtered polymers at 100° C. in vacuum for 24 hr gave poly{1,4-phenyleneoxy-1,4-phenylene-3,6-bis[4-(n-octyloxy)phenyloxy]pyromellitimide}.

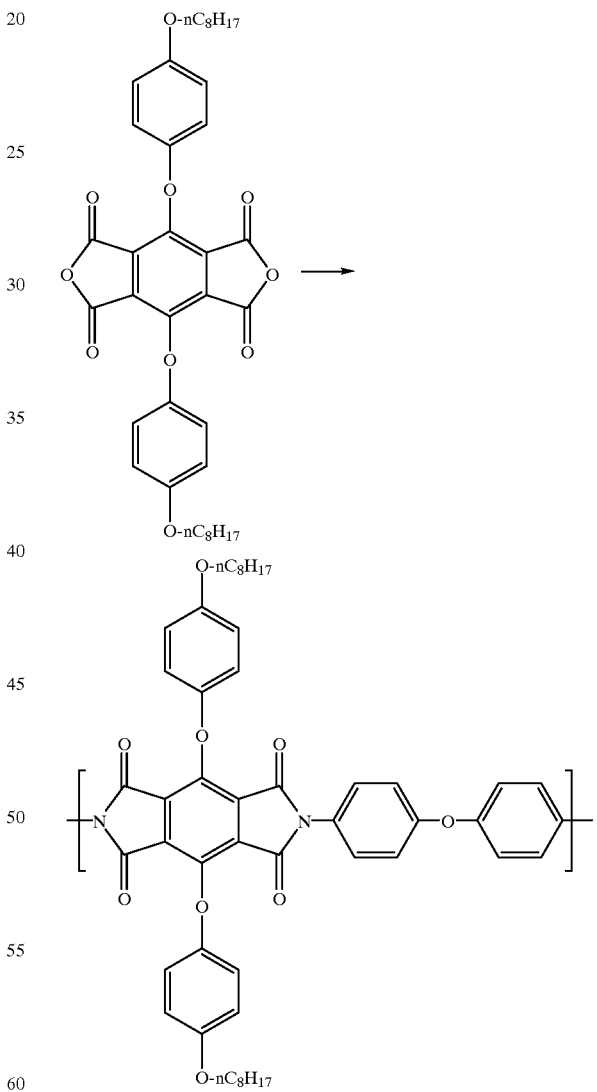

Yield: 99% Inherent viscosity (25° C., N-methylpyrrolidone, 0.2 g/dl): 0.76 dl/g Elemental analysis: C, 71.41%; H, 6.04%; N, 3.76%; IR (film, cm$^{-}$): 2960~2830 (CH), 1778 & 1701 (imide I), 1598 & 1502 (aromatic C=C), 1392 (imide II); 1242 & 1186 (C—O—C), 725 (-(CH$_2$)$_4$-)

USE EXAMPLE 8

Synthesis of poly{1,4-phenylenemethylene-1,4-phenylene-3,6-bis[4-(n-octyloxy)phenyloxy]pyromellitimide}

Into 80 ml of N,N'-dimethylacetamide were dissolved 6.58 g (10 mmol) of 3,6-bis[4-(n-octyloxy)phenyloxy] pyromellitic dianhydride and 1.98 g (10 mmol) of 4,4'-methylenedianiline. Under nitrogen purging this solution was violently stirred for 72 hr at ambient temperature. As the polymerization reaction proceeds, the solution became viscous.

To the viscous solution were added 50 ml of acetic anhydride and 1 ml of triethylamine and stirred for further 24 hr at ambient temperature under nitrogen. purging. When this solution was dropped to 600 ml ethanol under violent stirring, reddish precipitates were formed After these precipitates were filtered and air-dried, they were thoroughly extracted by refluxing in 80 ml ethanol for 24 hr and then filtered. Drying the filtered polymers at 100° C. in vacuum for 24 hr poly{1,4-phenylenemethylene-1,4-phenylene-3,6-bis[4-(n-octyloxy)phenyloxy]pyromellitimide}.

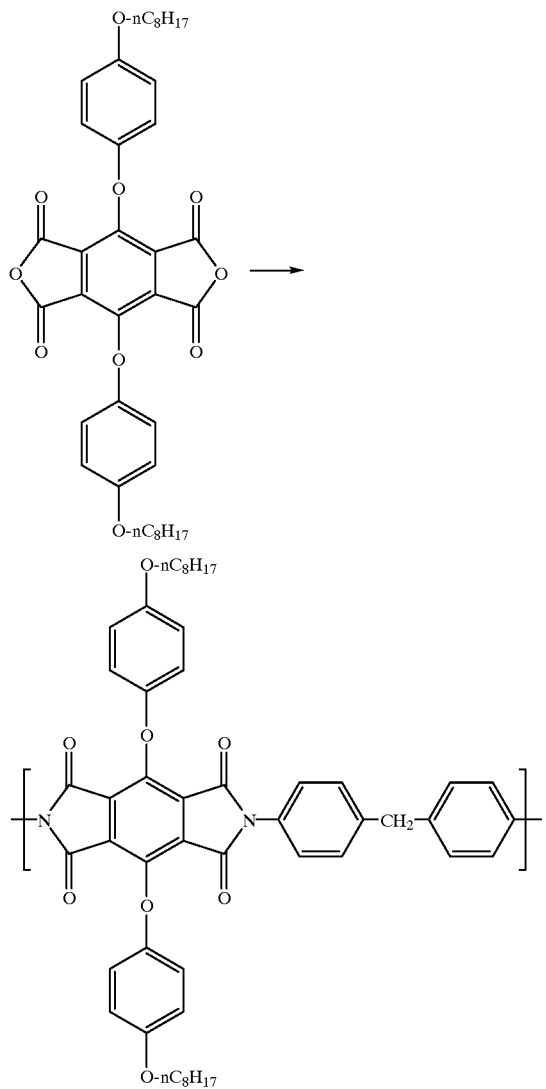

Yield: 99% Inherent viscosity (25° C., N-methylpyrrolidone, 0.2 g/dl): 0.64 dl/g Elemental analysis: C, 74.71%; H, 6.52%; N, 3.28%; IR (film, cm$^{-1}$): 2928~2856 (CH), 1776 & 1731 (imide I), 1610 & 1504 (aromatic C=C), 1390 (imide II), 1245 & 1186 (C—O—C), 724 (-(CH$_2$)$_4$-)

USE EXAMPLE 9

Synthesis of poly{1,4-phenylenecarbony-1,4-phenylene-3,6-bis[4-(n-octyloxy)phenyloxy]pyromellitimide}

Into 80 ml of N-methylpyrrolidone were dissolved 6.58 g (10 mmol) of 3,6-bis[4-(n-octyloxy)phenyloxy]pyromellitic dianhydride and 2.12 g (10 mmol) of 4,4'-diaminobenzophenone. Under nitrogen purging this solution was violently stirred for 72 hr at ambient temperature. As the polymerization reaction proceeds, the solution became viscous.

To the viscous solution were added 50 ml of acetic anhydride and 1 ml of triethylamine and stirred for further 24 hr at ambient temperature under nitrogen purging. When this solution was dropped to 600 ml ethanol under violent stirring, reddish precipitates were formed. After these precipitates were filtered and air-dried, they were thoroughly extracted by refluxing in 80 ml ethanol for 24 hr and then filtered. Drying the filtered polymers at 100° C. in vacuum for 24 hr gave poly{1,4-phenylenemethylene-1,4-phenylene-3,6-bis[4-(n-octyloxy)phenyloxy]pyromellitimide}.

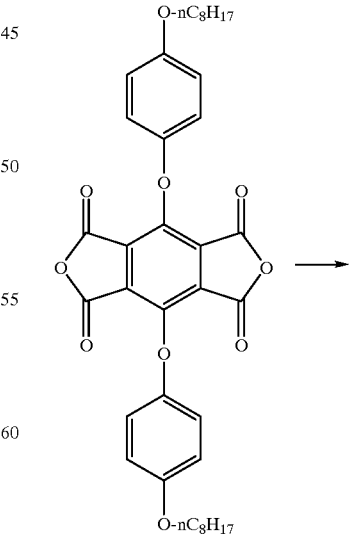

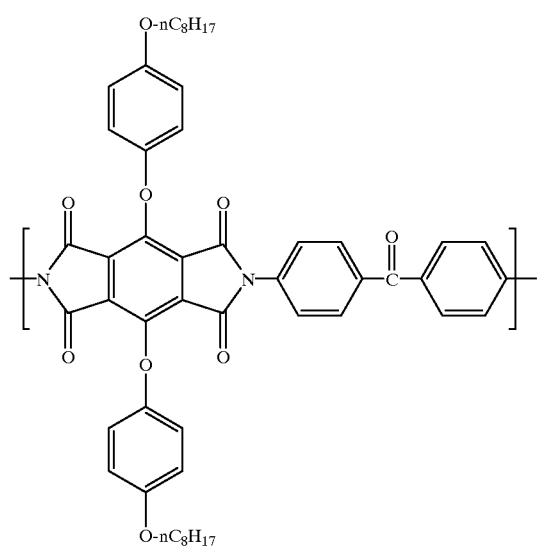

Yield: 99% Elemental analysis: C, 73.47%; H, 6.05%; N, 3.86%; IR (film, cm$^{-1}$): 2925~2860 (CH), 1778 & 1731 (imide I), 1664 (C=O), 1604 & 1504 (aromatic C=C), 1392 (imide II), 1245 & 1186 (C—O—C), 725 (-(CH$_2$)$_4$-)

USE EXAMPLE 10

Synthesis of poly{1,4-phenylene(hexafluoro)isopropylidene-1,4-phenylene-3,6-bis[4-(n-octyloxy)phenyloxy]pyromellitimide}

Into 80 ml of dimethylsulfoxide were dissolved 6.58 g (10 mmol) of 3,6-bis[4-(n-octyloxy)phenyloxy]pyromellitic dianhydride and 3.34 g (10 mmol) of 4,4'-hexafluoroisopropylidenedianiline. Under nitrogen purging this solution was violently stirred for 60 hr at ambient temperature. As the polymerization reaction proceeds, the solution became viscous.

To the viscous solution were added 50 ml of acetic anhydride and 1 ml of triethylamine and stirred for further 24 hr at ambient temperature under nitrogen purging. When this solution was dropped to 600 ml ethanol under violent stirring, reddish precipitates were formed. After these precipitates were filtered and air-dried, they were thoroughly extracted by refluxing in 80 ml ethanol for 24 hr and then filtered. Drying the filtered polymers at 100° C. in vacuum for 24 hr gave poly{1,4-phenylene(hexafluroro)isopropylidene-1,4-phenylene-3,6-bis[4-(n-octyloxy)phenyloxy]pyromellitimide}.

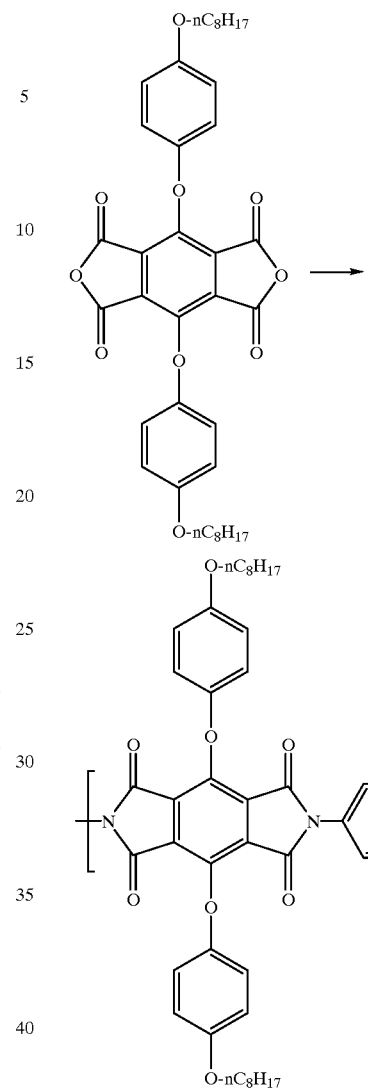

Yield: 99% Elemental analysis: C, 66.57%; H, 5.57%; N, 2.81%; F, 12.50%; IR (KBr, cm$^{-1}$): 2936~2856 (CH), 1778 & 1732 (imide I), 1664 (C=O), 1612 & 1506 (aromatic C=C), 1390 (imide II), 1250 & 1187 (C—O—C), 725 (-(CH$_2$)$_4$-)

To illustrate distinctively enhanced solubilities of the polyimides prepared in the Use Examples 1 to 10, their solubilties were compared with those of poly[3,6-bis(Q)pyromellitimide]s, where Q is bromo, fluoro, chloro, trifluoromethyl, phenyl or oxyphenyl.

All the polyimides prepared in Use Examples 1 to 10 were highly soluble in N-methylpyrrolidone even at room temperature and in dimethylsulfoxide, N,N-dimethylacetamide, N,N'-dimethylformamide, 1,2-dimethoxyethane and hexamethylphosphoramide on heating, whereas the poly[3,6-bis(Q)pyromellitimide]s prepared from 3,6-bis(Q)pyromellitc dianhydride and the same diamines used in Use Examples 1 to 10, such as 1,4-phenylenediamine, 4,4'-(3,3'-dimethyl)

biphenylenediamine, 4,4'-oxydianiline, 4,4'-methylenedianiline and 4,4'-diaminobenzophenone, were completely insoluble, even on heating, in any of the solvents named above. The single exception was the polyimide derived from 3,6-bis(phenyloxy)pyromelltic dianhydride and 4,4'-hexafluoroisopropylidenedianiline. This one showed a slight solubility in N-methylpyrrolidone on heating.

Accordingly, in comparison to the poly[3,6-bis(Q)pyromellitimide]s, the polyimides prepared in Examples 1 to 10 have distinctively enhanced solubilities in organic solvents, when the same diamines are incorporated in both the polyimides chains. These high solubilities can provide direct processing methods with the polyimides, without passing over complex imidization of the precursors such as poly(amic acid)s or poly(amic ester)s.

As clearly illustrated and demonstrated as aboves, the present invention provides 3,6-bis[4-(alkyloxy)phenyloxy]pyromellitic dianhydrides and a process for preparing the said compounds. Though Use Examples only for preparation of polyimides are shown in the present invention, 3,6-bis[4-(alkyloxy)phenyloxy]pyromellitic dianhydrides represented in formula I are also useful as monomers for the synthesis of ladder poly(imidazopyrrolone)s and crosslinked polyamides and polyesters. Particularly polyimides derived from the compounds of formula I, when diamines as their reaction partners are optionally selected, have generally so much enhanced solubilities in organic solvents that they can be processed directly, without passing over complex imidization reaction of the precursors.

What is claimed is:

1. 3,6-Bis[4-(alkyloxy)phenyloxy]pyromellitic dianhydride represented as the following formula I:

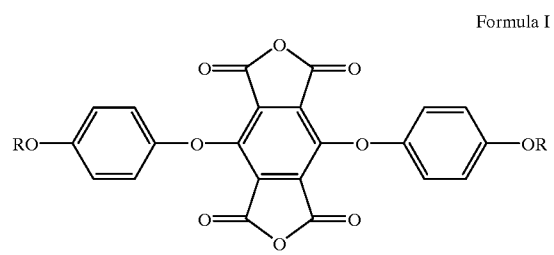

Formula I wherein
R is $C_{1-24}$ alkyl.

2. 3,6-Bis[4-(alkyloxy)phenyloxy]pyromellitic dianhydride of claim 1, wherein R is selected from the group consisting of methyl, ethyl, n-propyl, isopropyl, n-butyl, isobutyl, t-butyl, n-pentyl, isopentyl, 3-methylpentyl, n-hexyl, isohexyl, 2-ethylhexyl n-heptyl, isoheptyl, n-octyl, isooctyl, n-nonyl, n-decyl, isodecyl, n-undecyl, isoundecyl, n-dodecyl, isododecyl, n-tetradecyl, n-hexadecyl, n-octdadecyl, n-eicosyl, n-docosyl and n-tetracosyl.

3. A process for preparing 3,6-Bis[4-(alkyloxy)phenyloxy]pyromellitic dianhydride of claim 1, which comprises the following steps of:

(i) dissolving N,N'-diphenyl-3,6-bis(halogeno)pyromellitic diimide(A) and sodium 4-(alkyloxy)phenolate(B) in an organic solvent and reacting in the presence or absence of a base for 1 to 72 hrs, to obtain N,N'-diphenyl-3,6-bis[4-(alkyloxy)phenyloxy]pyromellitic diimide(C);

(ii) hydrolyzing N,N'-diphenyl-3,6-bis[4-(alkyloxy)phenyloxy]pyromellitic diimide(C) to obtain N,N'-diphenyl-3,6-bis[4-(alkyloxy)phenyloxy]pyromellitic acid(D); and, (iii) cyclodehydrating N,N'-diphenyl-3,6-bis[4-(alkyloxy)phenyloxy]pyromellitic acid(D) to produce N,N'-diphenyl-3,6-bis[4-(alkyloxy)phenyloxy]pyromellitic dianhydride represented as formula I:

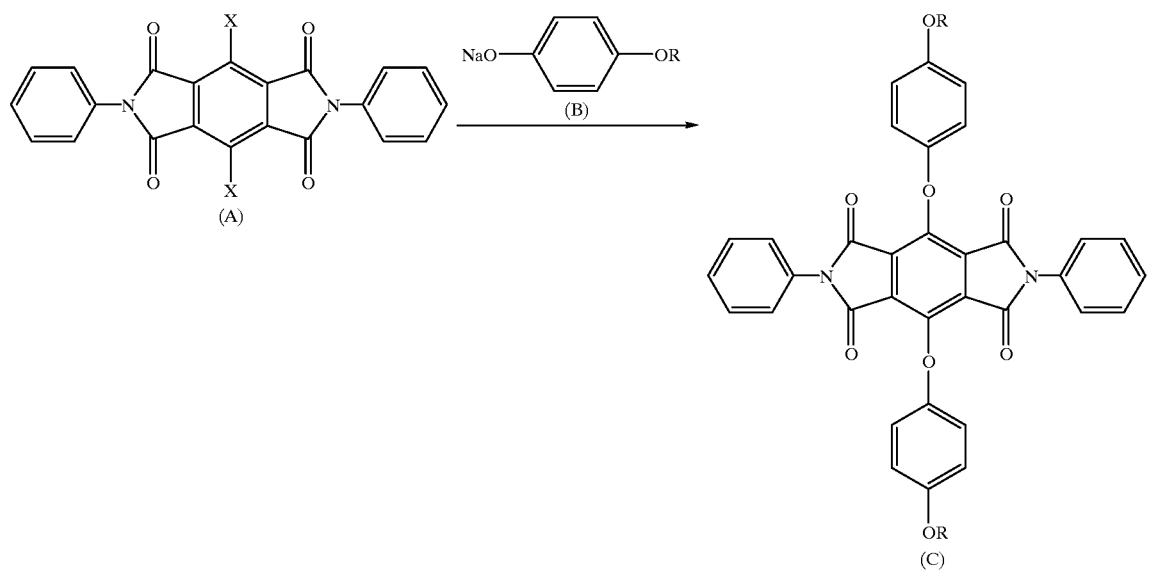

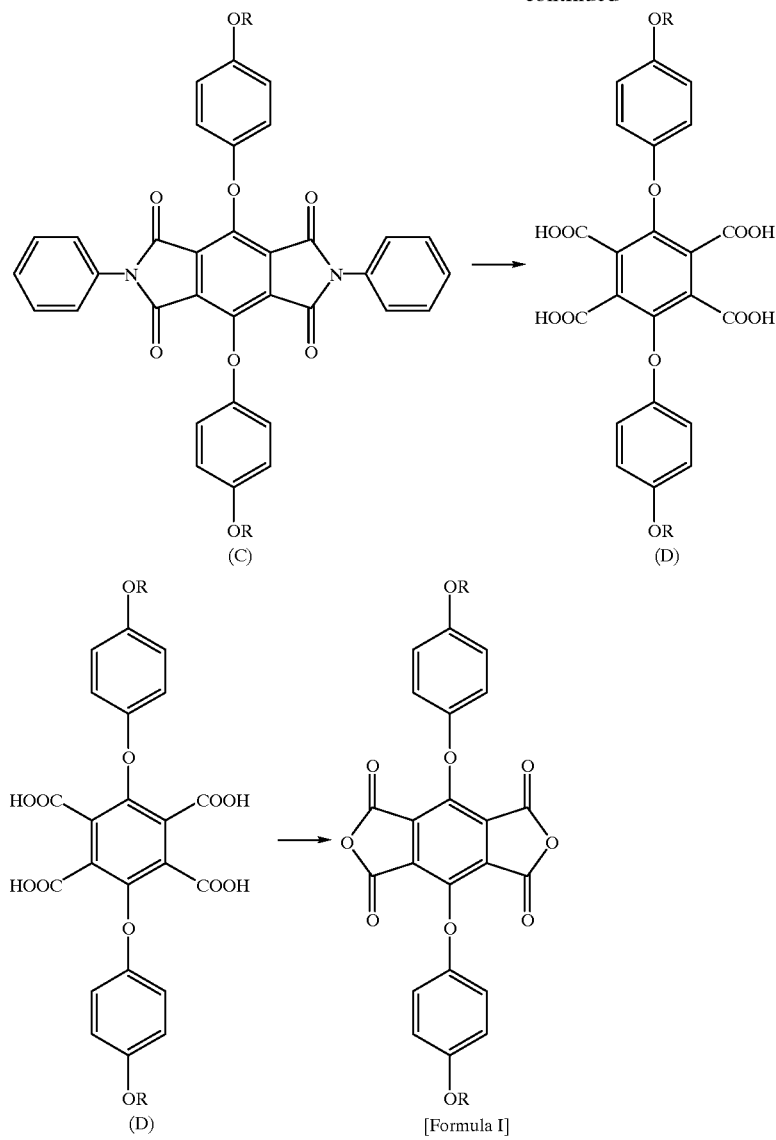

wherein,

X is F, Cl, Br or I; and,

R is $C_{1-24}$ alkyl.

4. The process of claim 3, wherein N,N'-diphenyl-3,6-bis(halogeno)pyromellitic diimide(A) is reacted with sodium 4-(alkyloxy)phenolate(B) at a temperature of −60° C. to boiling point of the organic solvent when X is F or I.

5. The process of claim 3, wherein N,N'-diphenyl-3,6-bis(halogeno)pyromellitic diimide(A) is reacted with sodium 4-(alkyloxy)phenolate(B) at a temperature of −40° C. to the boiling point of the organic solvent when X is Br or Cl.

6. The process of claim 3, wherein the organic solvent is selected from the group consisting of dimethylsulfoxide, N,N'-dimethylformamide, N,N'-dimethylacetamide, N-methylpyrrolidone, 1,2-dimethoxyethane and hexamethylphosphoramide.

7. The process of claim 3, wherein the base is selected from the group of pyridine, trimethylamine, triethylamine, tributylamine, N,N'-dimethylaniline, triethylenediamine, NaH, $NaOCH_3$, $NaOC_2H_5$, $NaO(n-C_3H_7)$, NaOH, KOH, and $Na_2CO_3$.

8. The process of claim 3, wherein N,N'-diphenyl-3,6-bis[4-(alkyloxy)phenyloxy]pyromellitic diimide(C) is hydrolyzed into N,N'-diphenyl-3,6-bis[4-(alkyloxy)phenyloxy]pyromellitic acid(D) by acidic or basic catalysts.

9. The process of claim 3, wherein the N,N'-diphenyl-3,6-bis[4-(alkyloxy)phenyloxy]pyromellitic acid(D) is cyclodehydrated by acetic anhydride.

10. The process of claim 3, wherein the N,N'-diphenyl-3,6-bis[4-(alkyloxy)phenyloxy]pyromellitic acid(D) is cyclodehydrated by thermal treatment.

11. The process of claim 3, wherein R is selected from the group consisting of methyl, ethyl, n-propyl, isopropyl, n-butyl, isobutyl, t-butyl, n-pentyl, isopentyl, 3-methylpentyl, n-hexyl, isohexyl, 2-ethylhelxyl, n-heptyl, isoheptyl, n-octyl, isooctyl, n-nonyl, n-decyl, isodecyl, n-undecyl, isoundecyl, n-dodecyl, isododecyl, n-tetradecyl, n-hexadecyl, n-octadecyl, n-eicosyl, n-docosyl, and n-tetracosdyl.

* * * * *